United States Patent [19]

Köhler

[11] Patent Number: 4,822,565
[45] Date of Patent: Apr. 18, 1989

[54] CARRIER DEVICE FOR IMMUNOLOGICAL ASSAY

[76] Inventor: Dora Köhler, Kreutzer Weg 11, D-1000 Berlin 45, Fed. Rep. of Germany

[21] Appl. No.: 710,123

[22] Filed: Mar. 11, 1985

[30] Foreign Application Priority Data

Nov. 6, 1984 [DE] Fed. Rep. of Germany ....... 3416933

[51] Int. Cl.⁴ ................. B01L 9/00; G01N 33/543; G01N 33/548
[52] U.S. Cl. ........................... 422/57; 422/58; 422/104; 436/518; 436/530; 436/809; 436/810
[58] Field of Search ............... 436/530, 807, 809, 810; 422/56, 57, 58, 104; 427/2

[56] References Cited

U.S. PATENT DOCUMENTS

| | | | |
|---|---|---|---|
| 3,932,141 | 1/1976 | Beall et al. | 436/809 |
| 3,999,948 | 12/1976 | Deindoerfer et al. | 436/530 |
| 4,200,613 | 4/1980 | Alfrey et al. | 436/809 |
| 4,276,259 | 6/1981 | Eibl et al. | 436/809 |
| 4,331,650 | 5/1982 | Brewer et al. | 422/56 |

FOREIGN PATENT DOCUMENTS

| | | | |
|---|---|---|---|
| 8200058 | 1/1982 | Int'l Pat. Institute | 436/501 |
| 8303677 | 10/1983 | Int'l Pat. Institute | |
| 2099578 | 12/1982 | United Kingdom | 435/7 |

OTHER PUBLICATIONS

"Biotechnology Trademarks", in *Biotechnology*, Catalogue of Fischer Scientific Co., 1983, p. 97.
R. Hawkes et al., Analytical Biochemistry, 119, 142–147, 1982.
B. J. Walsh et al., *Journal Immunological Methods* 73, 139–145, 1984.

Primary Examiner—Sam Rosen
Assistant Examiner—David A. Saunders
Attorney, Agent, or Firm—Morgan & Finnegan

[57] ABSTRACT

A carrier coated with antibodies or antigens is proposed, which performs a serological reaction with human, animal or plant material to be investigated and which is received in a multi-well plate. The carrier is made from nitrocellulose or a material having the adsorption characteristics of nitrocellulose and its shape is adapted to the multi-well plate used for performing serological reactions and is introduced into the latter. A plastic reinforcing structure provides support for the coated carrier. The coated carrier is not completely bound to the plastic reinforcing structure, so that both sides of the carrier will be contacted by material in the multi-well plate.

2 Claims, 1 Drawing Sheet

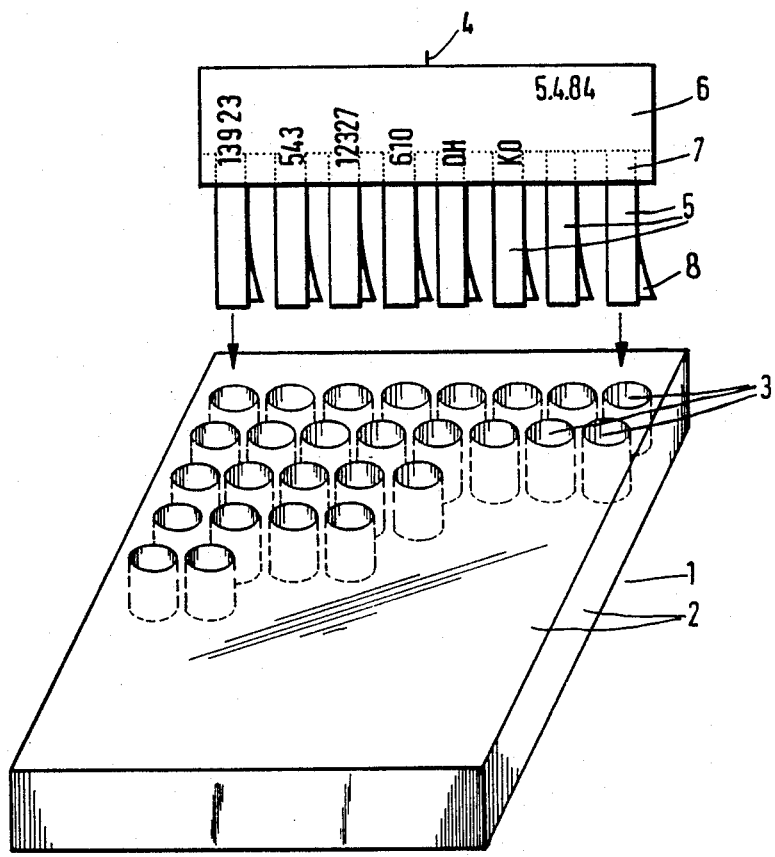

CARRIER DEVICE FOR IMMUNOLOGICAL ASSAY

BACKGROUND OF THE INVENTION

This invention relates to a carrier coated with antigens or antibodies, which performs a immunological reaction with human, animal or plant serum or body fluid received in a vessel.

The prior art discloses vessels for performing immunological reactions, which are known as MICROTITRE ® plates and which comprise a plurality of juxtaposed depressions arranged in a plastic card. Such MICROTITRE ® plates are coated in a complicated process with specially prepared antigens or antibodies. The serum to be investigated is placed in the depressions of the vessel and the antibodies present in the serum are bound to the antigens. In the further reaction process this binding action can be made clearly visible. This known process, in which the vessel simultaneously constitutes the carrier coated with the antigens and/or antibodies, suffers from several disadvantages.

During the stepwise immunological reaction process of the prior art, particularly through intermediate scavenging, the binding of the antigens and the antibodies is partly broken down, so that between about 30 and 70% of the originally bound antigens and antibodies are lost. Thus, standardized, reproducible test results are either not obtained or obtained only to a limited extent. Due to the fact that the carriers are constructed as vessels and that the juxtaposed depressions of the microtitre plate can only be coated in each case with one type of antigen, the general use of immunological methods for early, rapid and differential diagnosis of diseases and their pathogenic agents is possible only with difficulty. Due to the high material and technical expenditure, the production of carriers in vessel form is extremely cost-inventive. This additionally restricts the use of the prior art carrier.

Thus, it is an object of the present invention provides a carrier coated with antigens and/or antibodies for immunological reactions in connection with vessels used in serology which can be manufactured with low technical and material expenditure and which is easy to use. It is an additional object to provide a carrier which gives test results that are standardizable and reproducible, so as to permit early, rapid and differential diagnosis of diseases and pathogenic agents.

SUMMARY OF THE INVENTION

According to the present invention these problems are solved by the characterizing features described in the claims. A carrier is coated with antigens or antibodies. It is placed in a vessel with human, animal or plant material to be tested and the carrier is subjected to a immunological reaction. The carrier is formed from a material having the adsorption characteristics of nitrocellulose and the structural characteristics of nitrocellulose. Nitrocellulose has a relatively high degree of unspecific protein binding due to surface adsorption. The surface adsorption characteristic is theoretically due to hydrophobic and electrostatic, or ionic, bonding.

Due to the fact that nitrocellulose is used as the carrier and is coated with antigens and/or antibodies and due to the fact that the shape of the nitrocellulose can be adapted to the standard immunological vessels by cutting or the like, a broad range of uses and improved practicability through reduced costs is possible for doctors, in clinics and in laboratories. Through the use of the carrier according to this invention, simple differential diagnosis is possible. For example, different antigens or antibodies can be used with a MICROTITRE ® plate which is formed having a plurality of depressions for receiving the carriers containing serum and/or body juices.

The carrier according to this invention binds antigens and antibodies of different origins in a complete and durable manner without any complicated preparation. During the steps of the immunological reaction there are no antigen and antibody losses, so that standardized, reproducible test results can be obtained.

The carriers of this invention can be produced with limited technical and material expenditure, so that the production costs are much lower than those of the prior art carriers. The carriers of this invention are coated with antigens and/or antibodies and can be stored for long periods without any activity loss.

Other advantages, further developments and improvements of the carrier of this invention are possible as a result of the measures given in the independent and dependent claims and will become apparent in the description contained herein. The invention is described in greater detail hereinafter relative to non-limiting embodiments.

BRIEF DESCRIPTION OF THE DRAWING

The attached FIGURE shows a vessel in serological testing called a MICROTITRE ® microtitre plate and a perspective view of a carrier used therewith.

DETAILED DESCRIPTION OF THE PREFERRED EMBODIMENTS

The drawing shows a vessel 1 used in serological testing, called a MICROTITRE ® plate.

Vessel 1 has a plurality of depressions 3 arranged in a matrix in a plastic frame 2. The depressions 3 contain the human, animal or plant material to be tested and which can be serum or body fluids, such as urine, cerebrospinal fluid, blood, plant fluids or the like.

Carrier 4 is comb-like in appearance and comprises several strips 5, which are held in a holding member 6. The strips 5 are made from nitrocellulose, or some other material having absorption characteristics corresponding to those of nitrocellulose, or from structural and chemical analogs. They are coated with antibodies and/or antigens after the nitrocellulose is cut to size and, in the represented embodiment, placed in strip form. For example, the holding member 6 can be a plastic sheet, to which the strips 5 are secured in spaced manner by means of adhesive tapes 7. The holding member 6 can be labelled with data regarding the material to be tested and the like. For reinforcing and for protecting the strips 5 from damage, plastic strips 8 corresponding to the shape of strips 5 can be provided and on one side act as a support on being placed with strip 5 in holding member 6. As a function of the construction, the strips 5 are coated with the same or different types of antigens and/or antibodies.

The strips, which are, in each case, pretreated, are placed in depressions 3 containing the human, animal or plant material to be tested. The immunological reaction takes place on the carrier, on which the antibodies or antigens present in the material to be tested are bound to the antibodies or antigens on the carrier. The strips are treated with a reagent, e.g. Fast Red, or a like reagent in conjunction with naphthol, which is subject to a color change as a result of the immunological reactions. The reaction result can be observed optically, photometrically or microscopically as a result of this color change of carrier 4. The nature of the coloring of carrier 4 represents the test result.

In the described embodiment, vessel 1 is in the form of a MICROTITRE ® Plate and carrieris provided with a plurality of juxtaposed strips 5. However, it would obviously also be possible to provide other vessels, e.g. those with a depression and individual strips of nitrocellulose in another form.

For performing the immunological reactions, the material to be tested is placed in the depressions and the immunological reaction takes place on the individual carriers in the manner described hereinbefore.

What is claimed is:

1. A device adapted for use with a multi-well plate with individual wells for performing immunological assays, said device comprising
    (a) a holding member,
    (b) a flexible carrier and
    (c) a plastic reinforcing structure; said flexible carrier and said plastic reinforcing structure being attached to said holding member;
    said flexible carrier comprising a plurality of strips formed of nitrocellulose or nitrocellulose-like material having the absorption characteristics of nitrocellulose; said strips being arranged in comb-like, spaced fashion and being coated with antigens or antibodies and being capable of being immersed into individual wells of a multi-well plate;
    said plastic reinforcing structure comprising a plurality of strips arranged in a comb-like, spaced fashion and being capable of being immersed into individual wells of a multi-well plate;
    wherein each one of the plurality of flexible carrier strips is in a juxtaposed position relative to a plastic reinforcing strip but not completely bound thereto, so that both sides of the carrier strip will be contacted by the material in the wells and the plastic reinforcing strips will serve as a mechanical support.

2. A device according to claim 1 wherein said flexible carrier is nitrocellulose.

* * * * *